(12) United States Patent
Nakamura

(10) Patent No.: US 10,813,623 B2
(45) Date of Patent: Oct. 27, 2020

(54) ULTRASONIC DEVICE, ULTRASONIC APPARATUS, AND THICKNESS DESIGN METHOD

(71) Applicant: Seiko Epson Corporation, Tokyo (JP)

(72) Inventor: Tomoaki Nakamura, Shiojiri (JP)

(73) Assignee: Seiko Epson Corporation (JP)

( * ) Notice: Subject to any disclaimer, the term of this patent is extended or adjusted under 35 U.S.C. 154(b) by 387 days.

(21) Appl. No.: 15/817,665

(22) Filed: Nov. 20, 2017

(65) Prior Publication Data

US 2018/0146949 A1 May 31, 2018

(30) Foreign Application Priority Data

Nov. 29, 2016 (JP) ................. 2016-231418

(51) Int. Cl.
| | |
|---|---|
| *B06B 1/06* | (2006.01) |
| *A61B 8/00* | (2006.01) |
| *G01N 29/22* | (2006.01) |
| *A61B 8/08* | (2006.01) |
| *G01N 29/06* | (2006.01) |
| *G01N 29/24* | (2006.01) |
| *G01N 29/32* | (2006.01) |

(52) U.S. Cl.
CPC .......... *A61B 8/4444* (2013.01); *A61B 8/4272* (2013.01); *A61B 8/4494* (2013.01); *A61B 8/5269* (2013.01); *A61B 8/54* (2013.01); *B06B 1/0607* (2013.01); *G01N 29/0672* (2013.01); *G01N 29/221* (2013.01); *G01N 29/2437* (2013.01); *G01N 29/32* (2013.01); *G01N 2291/02475* (2013.01); *G01N 2291/2697* (2013.01)

(58) Field of Classification Search
CPC ....... B06B 1/06; B06B 1/0603; B06B 1/0607; B06B 1/0622; A61B 8/4444; A61B 8/4272; A61B 8/4494
USPC ......................................... 310/322, 334, 335
See application file for complete search history.

(56) References Cited

U.S. PATENT DOCUMENTS

| | | |
|---|---|---|
| 6,776,758 B2 | 8/2004 | Peszynski et al. |
| 2004/0073118 A1 | 4/2004 | Peszynski et al. |
| 2006/0238067 A1* | 10/2006 | Dausch ................ B06B 1/0622 310/311 |
| 2010/0168583 A1 | 7/2010 | Dausch et al. |
| 2010/0179430 A1 | 7/2010 | Sano et al. |
| 2016/0033454 A1* | 2/2016 | Matsuda ............ G01N 29/2437 73/632 |

(Continued)

FOREIGN PATENT DOCUMENTS

| | | |
|---|---|---|
| JP | 06-105844 A | 4/1994 |
| JP | 2004-130137 A | 4/2004 |
| JP | 3745703 B2 | 2/2006 |

(Continued)

*Primary Examiner* — Derek J Rosenau
(74) *Attorney, Agent, or Firm* — Harness, Dickey & Pierce, P.L.C.

(57) ABSTRACT

An ultrasonic device includes: a substrate that is provided with a first surface and a second surface as a back surface of the first surface and has an opening opened from the first surface to the second surface; a support that blocks the opening on the first surface side; a vibrator provided on the support; and a metal membrane provided in an unopened region, which is not opened by the opening, on the second surface of the substrate.

10 Claims, 11 Drawing Sheets

(56) References Cited

U.S. PATENT DOCUMENTS

2016/0035963 A1    2/2016   Kurokawa
2016/0144402 A1    5/2016   Kandori

FOREIGN PATENT DOCUMENTS

| JP | 4118737 B2 | 7/2008 |
| JP | 2010-508888 A | 3/2010 |
| JP | 4602013 B2 | 12/2010 |
| JP | 2016-033937 A | 3/2016 |
| JP | 2016-097033 A | 5/2016 |
| WO | WO-2008-114582 A1 | 9/2008 |

* cited by examiner

ULTRASONIC DEVICE, ULTRASONIC APPARATUS, AND THICKNESS DESIGN METHOD

BACKGROUND

1. Technical Field

The present invention relates to an ultrasonic device, an ultrasonic apparatus, and a thickness design method.

2. Related Art

In recent years, an ultrasonic device that transmits and receives ultrasonic waves has been known (for example, see JP-A-2016-97033).

An ultrasonic device disclosed in JP-A-2016-97033 includes a plurality of cells provided with a vibrating membrane. In the ultrasonic device, the vibrating membrane is vibrated such that ultrasonic waves are transmitted, and vibration of the vibrating membrane is detected such that received ultrasonic waves are detected. In the ultrasonic device, a silicone rubber layer is provided on the cell, and an electrostatic shield is provided via the silicone rubber layer.

In the ultrasonic device, a capacitive transducer in which a first electrode and a second electrode are disposed to face each other at intervals in the cell is used. Therefore, the above electrostatic shield is provided, and thereby it is possible to reduce an occurrence of electrical coupling between the electrodes that configure the capacitive transducer by charge electrically charged to a subject when the ultrasonic device is caused to approach the subject.

In an apparatus disclosed in JP-A-2016-97033, the electrostatic shield is provided, and thereby an influence of noise is reduced in the capacitive transducer. However, JP-A-2016-97033 does not provide description of a thickness dimension or the like of the electrostatic shield, and a problem arises in that the electrostatic shield will interfere with ultrasonic waves which are transmitted and received in the ultrasonic device, and acoustic characteristics are degraded.

SUMMARY

An advantage of some aspects of the invention is to provide an ultrasonic device, an ultrasonic apparatus, and a thickness design method, the ultrasonic device capable of reducing noise due to external electromagnetic waves while an occurrence of degradation in acoustic characteristics is reduced.

An ultrasonic device according to an aspect of the invention includes: a substrate that is provided with a first surface and a second surface as a back surface of the first surface and has an opening opened from the first surface to the second surface; a support that blocks the opening on the first surface side; a vibrator provided on the support; and a metal membrane provided in an unopened region, which is not opened by the opening, on the second surface of the substrate.

In this aspect, the metal membrane is provided in the unopened region, which is a region in which the opening is not provided, on the second surface of the substrate. In such a configuration, whether the support is vibrated by the vibrator such that the ultrasonic waves are transmitted or the ultrasonic waves are received through the support, the metal membrane is not provided on a traveling path of the ultrasonic waves. Therefore, an occurrence of interference by the metal membrane with the transmission and reception of the ultrasonic waves is reduced. In addition, even in a case where electromagnetic waves are input from outside, the electromagnetic waves are not input to the vibrator when the metal membrane is provided. Hence, it is possible to reduce an influence of noise during the reception of the ultrasonic waves, for example.

It is preferable that the ultrasonic device of this aspect further includes an acoustic layer provided in the opening, the metal membrane is provided in the unopened region and a region of the acoustic layer on the second surface, and the metal membrane has a thickness dimension of 10 μm or larger and 200 μm or smaller in a thickness direction of the substrate.

In this aspect, the acoustic layer is provided in the opening, and the metal membrane is also provided on the acoustic layer, with which the opening is filled, as well as in the unopened region of the substrate. The metal membrane has the thickness dimension of 10 μm or larger and 200 μm or smaller.

In this aspect, the metal membrane is provided in a region of the acoustic layer, and thereby it is possible to more effectively reduce an amount of the electromagnetic waves from outside. On the other hand, in this manner, when the metal membrane is provided in the region of the acoustic layer on a traveling route of the ultrasonic waves, the metal membrane interferes with the transmission and reception of the ultrasonic waves. In this respect, in this aspect, the metal membrane has the thickness dimension of 10 μm or larger and 200 μm or smaller. In such a configuration, a decrease rate of relatively penetrating acoustic pressure of the ultrasonic waves is 0.5 or lower due to the metal membrane, and thus it is possible to reduce an occurrence of a significant decrease in transmission and reception efficiency of the ultrasonic waves.

In the ultrasonic device of this aspect, it is preferable that the metal membrane has the thickness dimension of 10 μm or larger and 100 μm or smaller.

In this aspect, it is more preferable that the metal membrane has the thickness dimension of 10 μm or larger and 100 μm or smaller. The metal membrane has the thickness dimension of 10 μm or larger. In this manner, it is possible to sufficiently absorb the electromagnetic waves, and it is possible to reduce an occurrence of a problem in which noise electromagnetic waves that have penetrated through the metal membrane is input to the vibrator, for example. In addition, when the metal membrane has the membrane-thickness dimension larger than 100 μm, a width of decrease (gradient) of the relatively penetrating acoustic pressure is steep, and thus acoustic characteristics of the ultrasonic waves are unstable. In this respect, the metal membrane has the membrane-thickness dimension of 100 μm or smaller, and thereby acoustic characteristics of the ultrasonic waves are unlikely to remarkably change. Thus, it is possible to provide the ultrasonic device having stable acoustic characteristics.

In the ultrasonic device of this aspect, it is preferable that the metal membrane is provided in the unopened region in the second surface, on an inner circumferential surface of the opening, and on a surface of the support, which faces the opening.

In this aspect, the metal membrane is provided in the unopened region in the second surface of the substrate, on an inner circumferential surface of the opening, and on a surface of the support, which faces the opening. As described above, the metal membrane provided in the unopened region on the second surface of the substrate has a weak influence on the transmission and reception of the ultrasonic waves. Similarly, the metal membrane provided on the inner circumferential surface of the opening does not interrupt the traveling of the ultrasonic waves and has a weak influence on the transmission and reception of the ultrasonic waves. In addition, the metal membrane provided on the support membrane vibrates along with the support membrane in accordance with transmission and reception processing of the ultrasonic waves. Therefore, the metal membrane has a sufficiently small thickness dimension to the extent that the metal membrane does not interfere with the vibration of the support membrane, and thereby it is possible to reduce an influence on the transmission and reception of the ultrasonic waves even with the metal membrane provided on the support membrane. In other words, also in this aspect, it is possible to reduce the occurrence of a decrease in the transmission and reception efficiency of the ultrasonic waves due to the metal membrane, and it is possible to cover abroad range with the metal membrane. Therefore, it is possible to further reduce an influence of noise from the electromagnetic waves.

In the ultrasonic device of this aspect, it is preferable that the metal membrane is provided to surround the opening in the unopened region.

In this aspect, the metal membrane is provided to surround the opening in the unopened region. As described above, the metal membrane provided in the unopened region on the second surface of the substrate has a weak influence on the transmission and reception of the ultrasonic waves. In addition, since the metal membrane is provided to surround the opening, for example, it is possible to intercept a noise component of the electromagnetic waves while the occurrence of the degradation of the acoustic characteristics is reduced, compared to a case where the metal membrane covers the opening. In other words, also in this aspect, it is possible to reduce the occurrence of a decrease in the transmission and reception efficiency of the ultrasonic waves due to the metal membrane, and it is possible to further reduce an influence on the transmission and reception of the ultrasonic waves while an influence of noise from the electromagnetic waves is reduced because the metal membrane is not provided in the opening.

It is preferable that the ultrasonic device of this aspect further includes an acoustic layer provided in the opening, and the acoustic layer has a surface that is continued flat to the metal membrane of the unopened region.

In this aspect, one surface of the acoustic layer provided in the opening is continued flat to a surface of the metal membrane without a step. Therefore, when an acoustic member such as an acoustic lens is bonded on the metal membrane and the acoustic layer, for example, it is possible to reduce an occurrence of a problem in which gases such as air are mixed between the acoustic layer and the acoustic member.

An ultrasonic apparatus according to an aspect of the invention includes: the ultrasonic device as described above; and a controller that controls the ultrasonic device.

In this aspect, the controller can perform transmission processing of controlling the transmission of the ultrasonic waves by the ultrasonic device or the reception processing of receiving the ultrasonic waves by the ultrasonic device. In addition, the controller can perform various types of processing such as forming an internal tomographic image of a measurement target based on a received signal obtained through the reception processing.

A thickness design method according to an aspect of the invention is a thickness design method of a metal membrane in an ultrasonic device that performs at least one of transmission and reception of ultrasonic waves and includes a substrate which is provided with a first surface and a second surface as aback surface of the first surface and has an opening opened from the first surface to the second surface, a support that blocks the opening on the first surface side, a vibrator provided on the support and a metal membrane provided in an unopened region, which is not opened by the opening, on the second surface of the substrate, the method including: designing a dimension of the metal membrane in a thickness direction of the substrate such that a decrease rate of relatively penetrating acoustic pressure of the ultrasonic waves is 0.5 or lower.

According to this aspect, the dimension of the metal membrane in the thickness direction of the substrate is designed to a dimension such that a decrease rate of relatively penetrating acoustic pressure of the ultrasonic waves is 0.5 or lower. In this configuration, a decrease rate of relatively penetrating acoustic pressure of the ultrasonic waves is 0.5 or lower due to the metal membrane, and thus it is possible to provide the metal membrane due to which it is possible to reduce the occurrence of a significant decrease in transmission and reception efficiency of the ultrasonic waves.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, an ultrasonic apparatus according to a first embodiment will be described with reference to figures.

Schematic Configuration of Ultrasonic Apparatus

Figure 1:
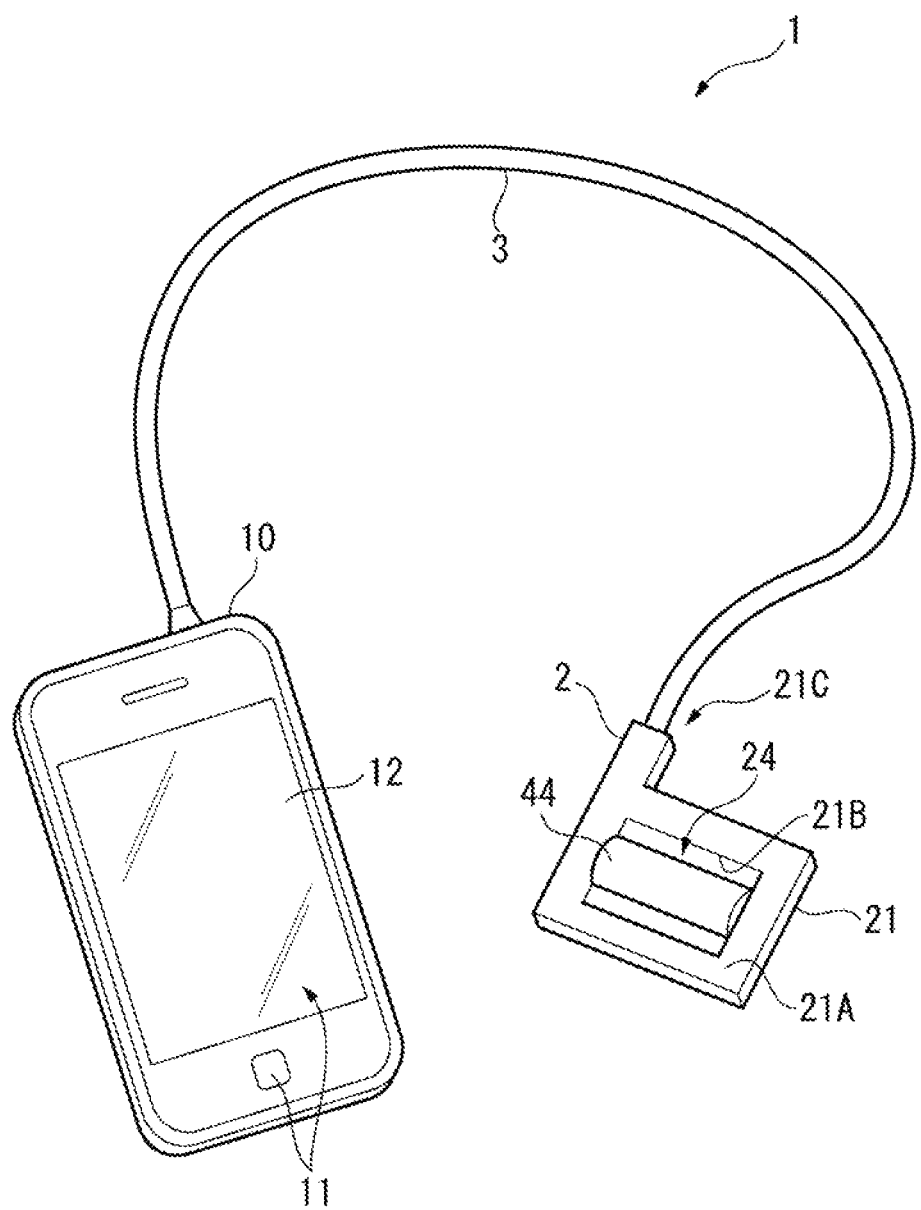
FIG. 1 is a perspective view illustrating a schematic configuration of an ultrasonic apparatus according to a first embodiment of the invention.
Figure 2:
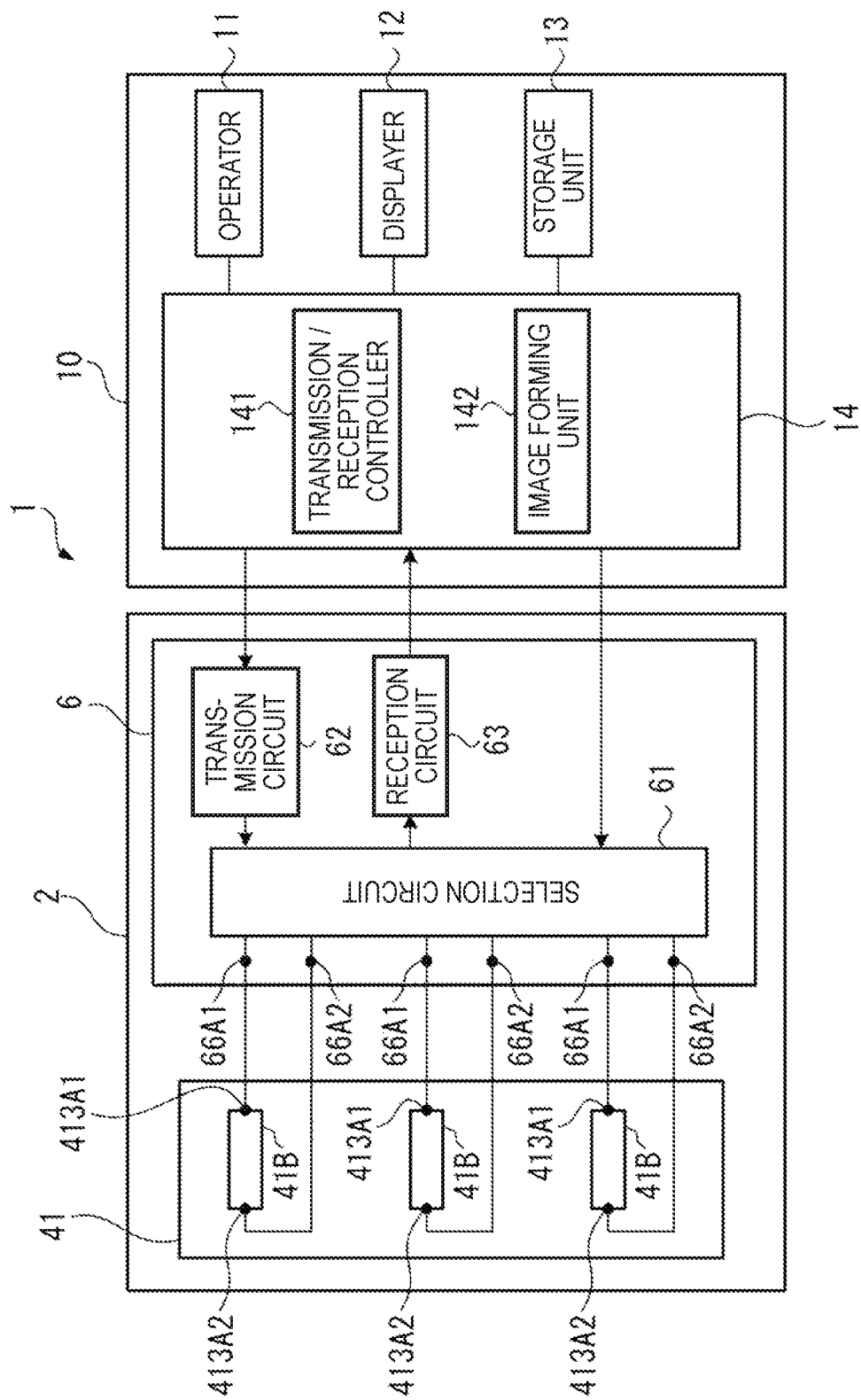
FIG. 2 is a block diagram illustrating a schematic configuration of the ultrasonic apparatus of the first embodiment.

FIG. 1 is a perspective view illustrating a schematic configuration of an ultrasonic apparatus 1 according to the embodiment. FIG. 2 is a block diagram illustrating a schematic configuration of the ultrasonic apparatus 1 of the embodiment.

As illustrated in FIG. 1, the ultrasonic apparatus 1 of the embodiment includes an ultrasonic probe 2 and a control device 10 that is electrically connected to the ultrasonic probe 2 via a cable 3.

In the ultrasonic apparatus 1, the ultrasonic probe 2 comes into contact with a front surface of a target subject (for example, a living body), and ultrasonic waves are emitted into the living body from the ultrasonic probe 2. In addition, the ultrasonic waves reflected from an organ in the target subject (living body) is received by the ultrasonic probe 2 and, for example, an internal tomographic image of the inside of the living body is acquired, based on a received signal thereof, or a state (for example, bloodstream or the like) of the organ in the living body is measured.

Configuration of Ultrasonic Probe

Figure 3:
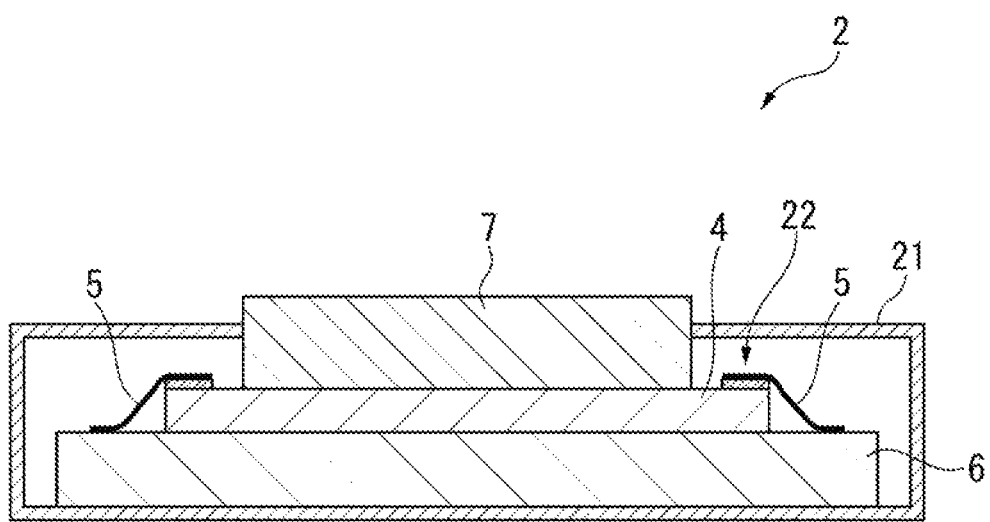
FIG. 3 is a sectional view illustrating a schematic configuration of an ultrasonic probe of the first embodiment.

FIG. 3 is a sectional view illustrating a schematic configuration of the ultrasonic probe 2.

The ultrasonic probe 2 is an ultrasonic module and includes a housing 21 and an ultrasonic sensor 22.

Configuration of Housing

As illustrated in FIG. 1, the housing 21 is formed to have a box shape with a rectangular shape in plan view, and accommodates the ultrasonic sensor 22. One surface (sensor surface 21A) orthogonal to the thickness direction of the housing 21 is provided with a sensor window 21B through which a part (acoustic lens 7 which will be described below) of the ultrasonic sensor 22 is exposed. In addition, a part (side surface in an example illustrated in FIG. 1) of the housing 21 is provided with a passing hole, and the cable 3 is inserted into the housing 21 via the passing hole. Although not illustrated, the cable 3 is connected to the ultrasonic sensor 22 (circuit substrate 6 which will be described below) inside the housing 21.

In the embodiment, a configurational example in which the ultrasonic probe 2 and a control device 10 are connected to each other by using the cable 3 is employed; however, the embodiment is not limited thereto and, for example, the ultrasonic probe 2 and the control device 10 may be connected to each other through wireless communication, or various types of configurations of the control device 10 may be provided in the ultrasonic probe 2.

Configuration of Ultrasonic Sensor

As illustrated in FIG. 3, the ultrasonic sensor 22 includes an ultrasonic device 4, the circuit substrate 6, and the acoustic lens 7. As will be described below, the circuit substrate 6 is provided with a driver circuit or the like for controlling the ultrasonic device 4, and, the ultrasonic device 4 is electrically connected to the circuit substrate 6 via a wiring member 5 such as a flexible substrate, for example. A surface of the ultrasonic device 4 on an ultrasonic transmission and reception side is provided with the acoustic lens 7, and the acoustic lens 7 is exposed outside from one surface side of the housing 21.

Configuration of Ultrasonic Substrate

Next, a configuration of an ultrasonic substrate 41 will be described.

Figure 4:
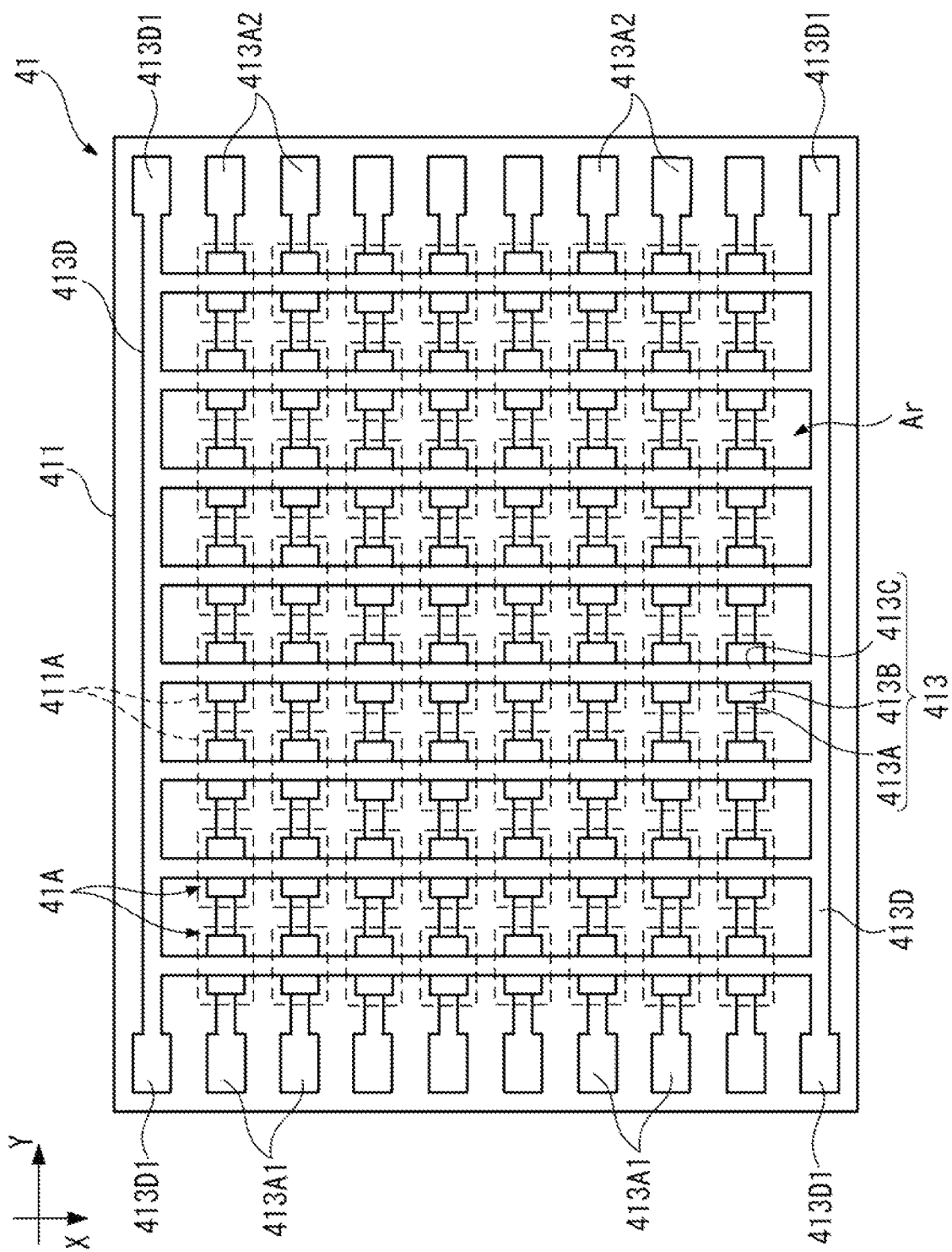
FIG. 4 is a plan view illustrating a schematic configuration of an ultrasonic substrate of the first embodiment.
Figure 5:
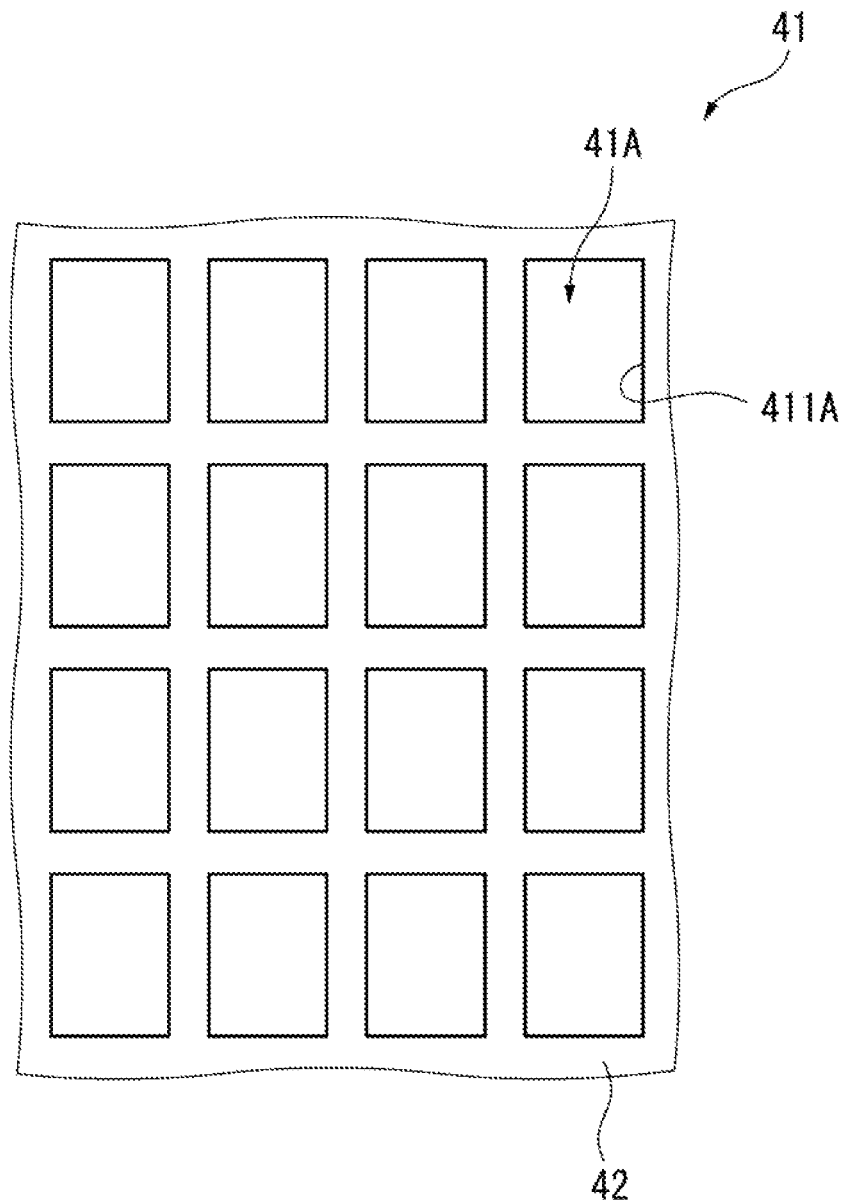
FIG. 5 is a plan view of the ultrasonic substrate of the first embodiment viewed from a side in an opposite direction to FIG. 4.

FIG. 4 is a plan view illustrating a schematic configuration of the ultrasonic substrate 41, and FIG. 5 is a plan view of a part of the ultrasonic substrate 41 viewed from a side in an opposite direction to FIG. 4.

The ultrasonic device 4 includes the ultrasonic substrate 41 and a metal membrane 42 (refer to FIG. 5) positioned on the ultrasonic substrate 41.

As illustrated in FIG. 4, on the ultrasonic substrate 41, a plurality of ultrasonic transducers 41A (ultrasonic element) are arranged in a two-dimensional array shape in an X direction (scan direction) and a Y direction (slice direction) which intersect with each other (in the embodiment, orthogonal as exemplified). Here, the plurality of ultrasonic transducers 41A arranged in the Y direction configure a transmission/reception row 41B (element group) of 1 CH (channel). In addition, a plurality of transmission/reception rows of the corresponding 1 CHs are disposed to be parallel in the Y direction, and thereby the ultrasonic substrate 41 is configured to have one-dimensional array structure. Here, a region, in which the ultrasonic transducers 41A are arranged, is referred to as an array region Ar.

In FIGS. 4 and 5, for convenience of description, the number of the arranged ultrasonic transducers 41A is small; however, more ultrasonic transducers 41A are actually arranged.

Figure 6:
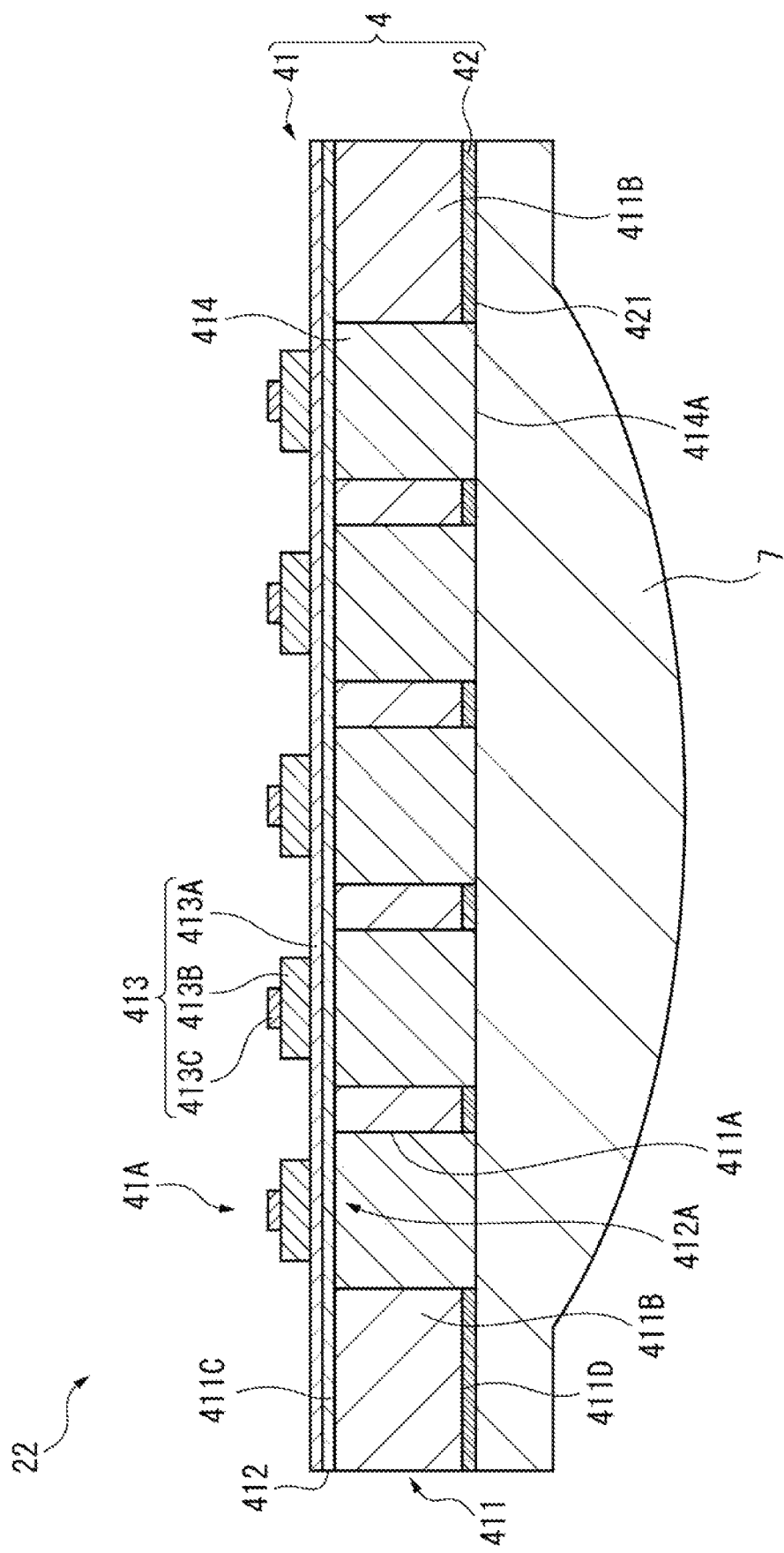
FIG. 6 is a sectional view obtained when the ultrasonic substrate of the first embodiment is cut in a Y direction.

FIG. 6 is a sectional view obtained when the ultrasonic sensor 22 (the ultrasonic device 4 and the acoustic lens 7) is cut to be parallel to the Y direction. Also in FIG. 6, for convenience of description, the number of the arranged ultrasonic transducers 41A is small; however, more ultrasonic transducers 41A are actually arranged.

As illustrated in FIG. 6, the ultrasonic substrate 41 is configured to include an element substrate 411, a support membrane 412 provided on a first surface 411C of the element substrate 411, and piezoelectric elements 413 provided on the support membrane 412.

For example, the element substrate 411 is configured of a semiconductor substrate made of Si or the like. The element substrate 411 is provided with openings 411A corresponding to the respective ultrasonic transducers 41A. In the embodiment, the respective openings 411A are opened from one end surface (first surface 411C) of the element substrate 411 to a second surface 411D which is a back surface of the first surface 411C, and are through-holes that penetrate through the substrate in the thickness direction thereof. The opening 411A is blocked by the support membrane 412 on the first surface 411C side.

A sealing plate (not illustrated) for reinforcing the element substrate 411 is disposed on the first surface 411C side of the element substrate 411 and is fixed by an adhesive member made of a resin or the like, for example.

The opening 411A is surrounded by partitions 411B on the periphery thereof and has a width dimension of about 30 μm in a short-side direction (for example, the X direction) of the corresponding opening 411A and a width dimension of about 60 μm in a long-side direction (for example, the Y direction) thereof. In addition, the partition 411B has a wall width of about 10 μm. The metal membrane 42, which will be described in detail below, is formed on the second surface 411D corresponding to a surface of the partition 411B.

In other words, the openings 411A having the maximum dimension of the opening width of about 70 μm are arranged at pitches of about 10 μm, and the metal membrane 42 is provided to surround the opening 411A.

In addition, the opening 411A is provided (filled) with an acoustic layer 414 on a side on which the support membrane 412 is not provided. Such an acoustic layer 414 has substantially the same acoustic impedance as that of the acoustic lens 7, and is brought into close contact with the support membrane 412 and the acoustic lens 7. In this manner, it is possible to deliver ultrasonic waves transmitted due to vibration of the support membrane 412 to the acoustic lens 7 via the acoustic layer 414, and it is possible to deliver ultrasonic waves incident from the acoustic lens 7 to the support membrane 412 via the acoustic layer 414.

For example, the support membrane 412 corresponds to a support of the invention, is configured of a laminated body or the like made of $SiO_2$, or $SiO_2$ and $ZrO_2$, and is provided to cover the entirety of the element substrate 411 on the first surface 411C side. In other words, the support membrane 412 is supported by the partition 411B that configures the opening 411A, and blocks the opening 411A on the first surface 411C side. A thickness dimension of the support membrane 412 is sufficiently smaller than a thickness dimension of the element substrate 411.

The piezoelectric elements 413 are provided on the support membrane 412 that blocks the openings 411A. For example, the piezoelectric elements 413 are configured of a stacked body in which a lower electrode 413A, a piezoelectric membrane 413B, and an upper electrode 413C are stacked from the support membrane 412 side.

Here, a portion of the support membrane 412, which blocks the opening 411A, configures a vibrating portion 412A, and the vibrating portion 412A and the piezoelectric elements 413 configure one ultrasonic transducer 41A (vibrator).

In such an ultrasonic transducer 41A, a rectangular voltage (drive signal) having a predetermined frequency is applied between the lower electrode 413A and the upper electrode 413C, and thereby the piezoelectric membrane 413B is bent. In this manner, the vibrating portion 412A is vibrated such that the ultrasonic waves are emitted. In addition, when the vibrating portion 412A is vibrated due to the ultrasonic waves reflected from a living body, a potential difference between the upper and lower side of the piezoelectric membrane 413B. In this manner, the potential difference generated between the lower electrode 413A and the upper electrode 413C is detected, and thereby it is possible to detect the received ultrasonic waves.

In addition, in the embodiment, as illustrated in FIG. 4, the lower electrode 413A is formed to have a linear shape in the Y direction, and connects the plurality of the ultrasonic transducers 41A that configure the transmission/reception row 41B of 1 CH. The lower electrode 413A is provided with a first terminal 413A1 on a −Y-side end portion (one end portion in a first direction) thereof, and a second terminal 413A2 on a +Y-side end portion (the other end portion in a first direction) thereof. The first terminal 413A1 and the second terminal 413A2 are both electrically connected to the circuit substrate 6.

In addition, the upper electrode 413C is formed to have a linear shape in the X direction, and connects the plurality of ultrasonic transducers 41A which are aligned in the X direction. Thus, ±X-side end portions of the upper electrode 413C are connected to a common electrode line 413D. The common electrode line 413D connects the plurality of upper electrodes 413C arranged in the Y direction to each other, and common terminals 413D1 which are electrically connected to the circuit substrate 6 are provided at the end portions of the common electrode line.

Configuration of Metal Membrane

The metal membrane 42 is configured of a metal membrane made of Al (aluminum) or the like. In a case where electromagnetic waves are input from outside, the metal membrane 42 reduces an occurrence of an input of the corresponding electromagnetic waves to the ultrasonic transducers 41A (vibrator). Such a metal membrane 42 is positioned in an unopened region that is not opened by the opening 411A on the second surface 411D which is a back surface of the first surface 411C of the ultrasonic substrate 41. In other words, the metal membrane 42 is provided on the partition 411B that forms the opening 411A on the second surface 411D of the ultrasonic substrate 41. Accordingly, in the embodiment, as illustrated in FIG. 5, the metal membrane 42 is provided to surround the opening 411A in plan view when the ultrasonic substrate 41 is viewed in the thickness direction of the substrate.

Specifically, since the metal membrane 42 is provided on the second surface 411D corresponding to the partition 411B, the metal membrane 42 has a width dimension of about 10 μm which is a wall width of the partition 411B described above. In addition, a dimension of the opening 411A in a direction parallel to the Y direction is about 30 μm as described above, and a dimension thereof in a direction parallel to the X direction is about 60 μm as described above. Hence, the metal membrane 42 is disposed on the partition 411B at a pitch distance of at least about 60 μm. In other words, the metal membrane 42 has a so-called mesh shape and is positioned on the second surface 411D.

The metal membrane 42 reduces a penetration amount of electromagnetic waves from outside through reflection of the electromagnetic waves from a front layer and absorption of the electromagnetic waves in the metal membrane 42. Of them, the penetration amount of the electromagnetic waves is reduced by the reflection.

Here, electromagnetic waves which are wanted to be cut off as noise in the embodiment are electromagnetic waves having frequency of 30 MHz to 1 GHz. For example, such electromagnetic waves have a wavelength of about 10 m in a case where the frequency is 30 MHz, and has a wavelength of 300 mm in a case where the frequency is 1 GHz. In order to achieve an electrostatic shield effect by the mesh-shaped metal membrane 42, mesh spacing needs to be shorter than a half wavelength of the electromagnetic waves.

In this respect, in the embodiment, the metal membrane 42 has the width dimension of about 10 μm and the maximum value of the pitch distance is 70 μm or smaller. Accordingly, the electromagnetic waves having the above frequency bandwidths do not penetrate through mesh holes, but it is possible to achieve the electromagnetic shield effect through reflection from or absorption to the metal membrane 42.

In addition, the metal membrane 42 is fixed to the partition 411B through a process of vapor deposition or the like, for example. The metal membrane 42 is formed to have a thickness dimension of 10 μm or larger.

The electromagnetic shield obtained by the metal membrane 42 is achieved due to shield effects mainly through reflection; however, it is possible to achieve a higher shield effect by absorbing the electromagnetic waves by the metal membrane 42 as well as the reflection.

Here, in the absorption of the electromagnetic waves by the metal membrane 42, the shield effect (attenuation loss A) is obtained from Expression (1).

$$A = 131.4 t \sqrt{f \mu \sigma} \tag{1}$$

In Expression (1), t represents a membrane-thickness dimension of the metal membrane 42, f represents a frequency of an electromagnetic wave of a cutting target, μ represents permeability of a membrane material of the metal membrane 42, and σ represents conductivity of the membrane material of the metal membrane 42. In the embodiment, the metal membrane 42 is formed of aluminum, and thus $\mu = 1.26 \times 10^{-6}$ (H/m), and σ is $3.96 \times 10^7$ (S/m).

In the ultrasonic measurement, in a case where an internal tomographic image of a living body is obtained, in order to reduce the occurrence of degradation of the image such as unclearness of an image which is a noise component, it is preferable to achieve the shield effect to the extent of 120 dB. In the embodiment, electromagnetic waves that can be converted into noise during the ultrasonic measurement are the electromagnetic waves having the frequency of 30 MHz to 1 GHz. The thickness dimension t of the metal membrane 42 has a relationship of t≥8 µm. In this manner, it is possible to achieve the shield effect, and the membrane-thickness dimension of the metal membrane is more preferably 10 µm or larger. For example, in a case where the metal membrane 42 has the membrane-thickness dimension of 10 µm, the shield effect is 51 dB with respect to the electromagnetic waves having the frequency f of 30 MHz, and is 294 dB with respect to the electromagnetic waves having the frequency f of 1 GHz. Hence, it is possible to achieve a sufficient shield effect.

In the embodiment, the metal membrane 42 is formed of aluminum; however, the material is not limited thereto, and, for example, the metal membrane may be formed of any metal such as silver, copper, nickel, gold, or the like. In other words, in the embodiment, the metal membrane 42 made of a metal material having a product of permeability µ and conductivity σ, which is 30 or higher, may be formed to have the membrane-thickness dimension of t=10 µm or larger. In such a configuration, it is possible to cut penetration of the electromagnetic waves having 30 MHz to 1 GHz which are a cause of noise.

Configuration of Acoustic Lens

The acoustic lens 7 efficiently propagates, to the living body which is the measurement target, the ultrasonic waves transmitted from the ultrasonic device 4, and efficiently propagates, to the ultrasonic device 4, the ultrasonic waves reflected from the living body. The acoustic lens 7 is disposed along a surface through which the ultrasonic device 4 transmits and receives the ultrasonic waves.

Here, as described above, the acoustic layer 414 is provided between the ultrasonic device 4 and the acoustic lens 7. After the metal membrane 42 is deposited on the element substrate 411, the acoustic layer 414 is formed when the opening 411A is filled with a liquid-phase material (for example, a liquid-phase silicone) that forms the acoustic layer 414. At this time, a front surface of the acoustic layer is leveled to be an evenly flat surface so as to flush with a front surface of the metal membrane 42 (a surface on an opposite side to the element substrate 411) by using a member such as a spatula having a linear shape. Hence, a surface 414A of the acoustic layer 414 on the opposite side to the element substrate 411 is a surface that is continued flat to a front surface 421 of the metal membrane 42 without a step.

In this manner, when the acoustic lens 7 is bonded to the front surface 421 of the metal membrane 42 and the surface 414A, an occurrence of a problem in which gases such as the air are sealed between the acoustic layer 414 and the acoustic lens 7 is reduced.

Configuration of Circuit Substrate

Next, the circuit substrate 6 will be described.

Back to FIG. 2, for example, the circuit substrate 6 includes a selection circuit 61, a transmission circuit 62 (signal output portion), and a reception circuit 63, as various types of circuits that drive the ultrasonic transducers 41A. In addition, the circuit substrate 6 includes a first input/output portion 66A1 that is connected to the first terminal 413A1 of the ultrasonic substrate 41, and a second input/output portion 66A2 that is connected to the second terminal 413A2.

Further, although not illustrated, the circuit substrate 6 includes a common input/output portion that is connected to the common terminal 413D1, a common voltage output portion that is connected to the common input/output portion and applies a common voltage to the common terminal 413D1, and the like.

The selection circuit 61 is connected to the transmission/reception row 41B of the ultrasonic substrate 41. In addition, the selection circuit 61 is connected to the transmission circuit 62 and the reception circuit 63.

The selection circuit 61 switches, based on the control by the control device 10, between transmission connection by which the ultrasonic transducers 41A (the transmission/reception row 41B) and the transmission circuit 62 are connected to each other and reception connection that connects the ultrasonic transducers 41A (the transmission/reception row 41B) and the reception circuit 63.

The transmission circuit 62 is a signal output portion that outputs a drive signal, and outputs the drive signal when the control device 10 controls to switch to the transmission connection. The drive signal is input to the transmission/reception rows 41B via the selection circuit 61, and thereby the ultrasonic transducers 41A are driven and the ultrasonic waves are emitted.

The reception circuit 63 processes the received signal input from the transmission/reception row 41B via the selection circuit 61 when the reception circuit is switched to the reception connection through the control by the control device 10. Specifically, the reception circuit 63 is configured to have a low noise amplifier circuit, for example, a voltage control attenuator, a programmable gain amplifier, a low pass filter, an A/D converter, or the like, converts the received signal into digital signal, removes a noise component, performs various types of signal processing such as amplification to a predetermined signal level, and then outputs the received signal to the control device 10 after processing.

Configuration of Control Device

For example, as illustrated in FIG. 2, the control device 10 is configured to include an operator 11, a displayer 12, a storage unit 13, and a controller 14. For example, the control device 10 may use a terminal device such as a tablet terminal, a smart phone, or a personal computer, and may be a dedicated terminal device for operating the ultrasonic probe 2.

The operator 11 is a user interface (UI) through which a user operates the ultrasonic apparatus 1, and can be formed of a touch panel, an operating button, a keyboard, a mouse, and the like which are provided on the displayer 12.

The displayer 12 is configured of a liquid crystal displayer or the like, and displays an image.

The storage unit 13 stores various types of programs and various types of data for controlling the ultrasonic apparatus 1.

The controller 14 is configured to have an arithmetic circuit such as a central processing unit (CPU), and the storage circuit such as a memory. The controller 14 performs reading of the various types of programs stored in the storage unit 13, thereby functioning as a transmission/reception controller 141 and an image forming unit 142, for example.

The transmission/reception controller 141 controls the selection circuit 61 and switches between the transmission connection and reception connection. In addition, the transmission/reception controller 141 controls generation and output processing of the drive signal with respect to the transmission circuit 62, and controls frequency setting, gain setting or the like of the received signal with respect to the reception circuit 63.

The image forming unit 142 generates an internal tomographic image (ultrasonic image) of a living body, based on the reception signal (image signal) received from the ultrasonic probe 2. In addition, the image forming unit 142 displays the generated internal tomographic image on the displayer 12.

Operational Effect of First Embodiment

The ultrasonic apparatus 1 according to the embodiment described above has the following effects.

In the embodiment, the second surface 411D of the ultrasonic substrate 41 is provided with the metal membrane 42 on the partition 411B which is a region, in which the opening 411A is not provided. In such a configuration, whether the support membrane 412 is vibrated by the piezoelectric element 413 such that the ultrasonic waves are transmitted or the ultrasonic waves are received through the support membrane 412, the metal membrane 42 is not provided on a traveling path of the ultrasonic waves. Therefore, an occurrence of interference by the metal membrane 42 with the transmission and reception of the ultrasonic waves is reduced. In addition, even in a case where the metal membrane 42 is provided, and thereby electromagnetic waves are input from outside, the corresponding electromagnetic waves are not input to the piezoelectric element 413. Hence, it is possible to reduce an influence of noise during the reception of the ultrasonic waves, for example.

In addition, regarding the internal tomographic image that is acquired from the ultrasonic probe 2 of the ultrasonic apparatus 1 and is displayed on the displayer 12 of the control device 10, it is possible to reduce an occurrence of disorganization of the image due to the noise component, unclearness, or the like.

In this embodiment, the metal membrane 42 is provided to surround the opening 411A in the partition 411B which is an unopened region. As described above, the metal membrane 42 provided on the second surface 411D corresponding to the partition 411B of the ultrasonic substrate 41 has a weak influence on the transmission and reception of the ultrasonic waves. In addition, since the metal membrane 42 is provided to surround the opening 411A, for example, it is possible to intercept a noise component of the electromagnetic waves while the occurrence of the degradation of the acoustic characteristics is reduced, compared to a case where the metal membrane 42 covers the opening 411A. In other words, it is possible to reduce the occurrence of a decrease in the transmission and reception efficiency of the ultrasonic waves due to the metal membrane 42, and it is possible to further reduce an influence on the transmission and reception of the ultrasonic waves while an influence of noise from the electromagnetic waves is reduced because the metal membrane 42 is not provided in the opening 411A.

In the embodiment, the acoustic layer 414 is formed to fill the opening 411A, and the acoustic layer 414 has the surface 414A that is continued flat to the front surface 421 of the metal membrane 42 without a step. Therefore, when the acoustic lens 7 or the like is bonded to the front surface 421 of the metal membrane 42 and the surface 414A, an occurrence of flowing of gases such as the air between the acoustic layer 414 and the acoustic lens 7 is reduced. Hence, it is possible to reliably fix the acoustic lens 7 on the ultrasonic device 4, and it is possible to reduce the occurrence of a decrease in the transmission and reception efficiency of the ultrasonic waves by the metal membrane 42.

In this embodiment, the controller 14 can perform transmission processing of controlling the transmission of the ultrasonic waves by the ultrasonic device 4 or the reception processing of receiving the ultrasonic waves by the ultrasonic device 4. In addition, the controller 14 can perform various types of processing such as forming of an internal tomographic image of a measurement target based on a received signal obtained through the reception processing, for example.

First Modification Example of First Embodiment

In the first embodiment, the metal membrane 42 is disposed to surround the opening 411A on the second surface 411D corresponding to the partition 411B of the ultrasonic substrate 41; however, the disposition is not limited thereto, and for example, a configuration in which the metal membrane 42 is only provided on an outer edge in the partition 411B (unopened portion), and a region extending in a direction parallel to the X direction may be employed.

Figure 7:
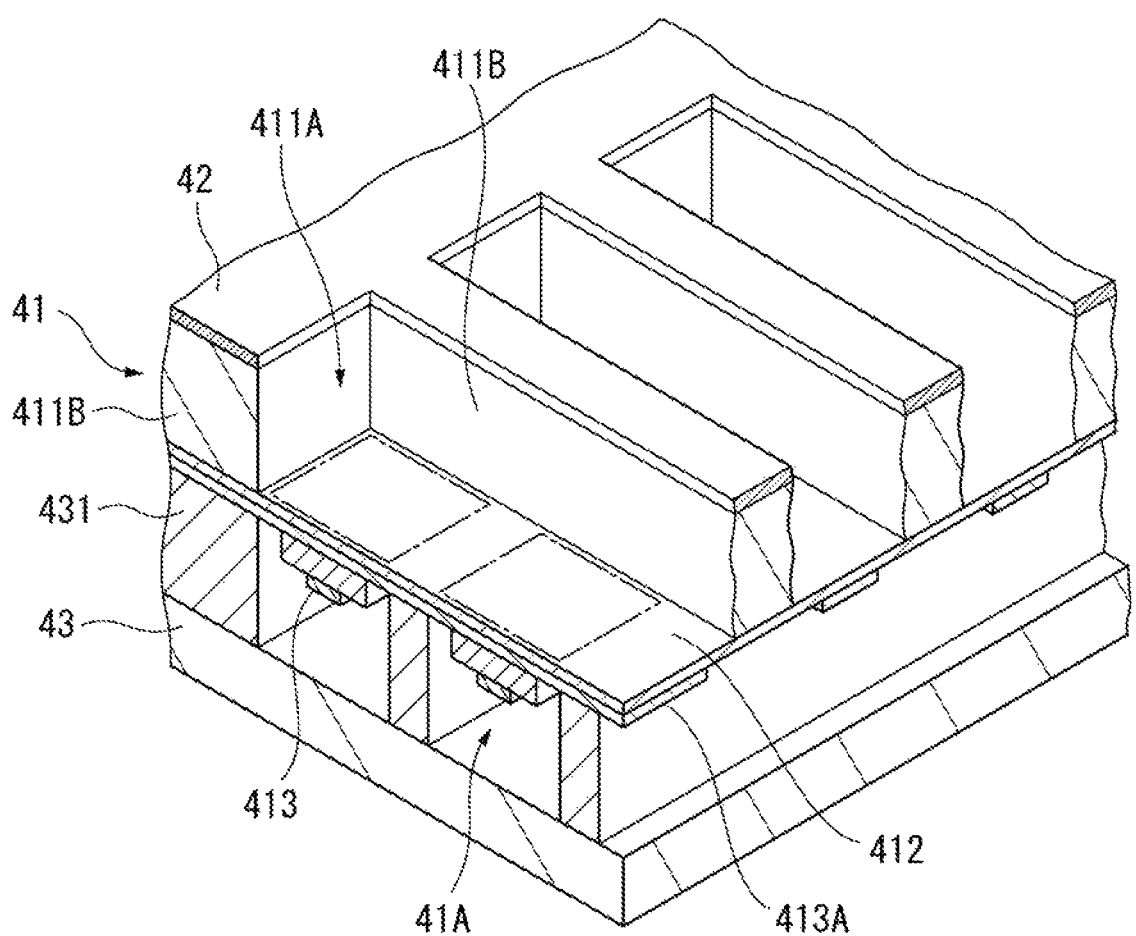
FIG. 7 is a perspective view illustrating a schematic configuration of an ultrasonic device according to a modification example of the first embodiment.

FIG. 7 is a perspective view illustrating a schematic configuration of the ultrasonic device 4 according to a modification example of the first embodiment.

In the first embodiment, the vibrating portion 412A of the ultrasonic transducers 41A is formed by the opening 411A (partition 411B) of the element substrate 411; however, as illustrated in FIG. 7, the vibrator may be configured to include the partition 411B and a resin member 431 for bonding a sealing plate 43.

In the modification example, the opening 411A has a longitudinal shape parallel to the Y direction and is disposed over the plurality of ultrasonic transducers 41A.

In addition, a plurality of the resin members 431 that bond the sealing plate 43 and the element substrate 411 are provided to be parallel to the X direction.

In such a configuration, the vibrating portion 412A of the ultrasonic transducers 41A is configured of a region of the support membrane 412 which is surrounded by a pair of adjacent partitions 411B and a pair of adjacent resin members 431.

In such a configuration, the metal membrane 42 is disposed on the partition 411B to surround the opening 411A that is long in the Y direction. In this case, the opening 411A has an opening width which is shorter than 150 μm in the Y direction. In this manner, it is possible to cut the electromagnetic waves of 30 MHz to 1 GHz without causing the waves to pass through a gap of the metal membrane 42.

Further, the metal membrane 42 may be provided to surround an opening group (a plurality of openings 411A) per 1 CH.

Effect of First Modification Example of First Embodiment

According to the modification example, since the metal membrane 42 is provided only on an outer edge and a region of the partition 411B which extends in a direction parallel to one direction (Y direction), it is possible to reduce an amount of vapor deposition of the metal membrane 42, compared to a case where the metal membrane 42 is provided on the entire region of the partition 411B. Also in this case, it is possible to achieve the same effects as those of the first embodiment.

In addition, since the ultrasonic device 4 has the sealing plate 43, the ultrasonic substrate 41 is reinforced, and thereby it is possible to protect the ultrasonic transducer 41A.

Second Embodiment

Next, a second embodiment of the invention will be described.

In the first embodiment described above, an example in which the metal membrane 42 is positioned on the partition 411B and on the second surface 411D of the ultrasonic substrate 41, that is, an example in which the metal membrane 42 is positioned on the partition 411B so as to surround the opening 411A, is described.

In this respect, the second embodiment differs from the first embodiment in that a metal membrane 42A is provided in a substantially entire region of the second surface 411D of the ultrasonic substrate 41.

Figure 8:
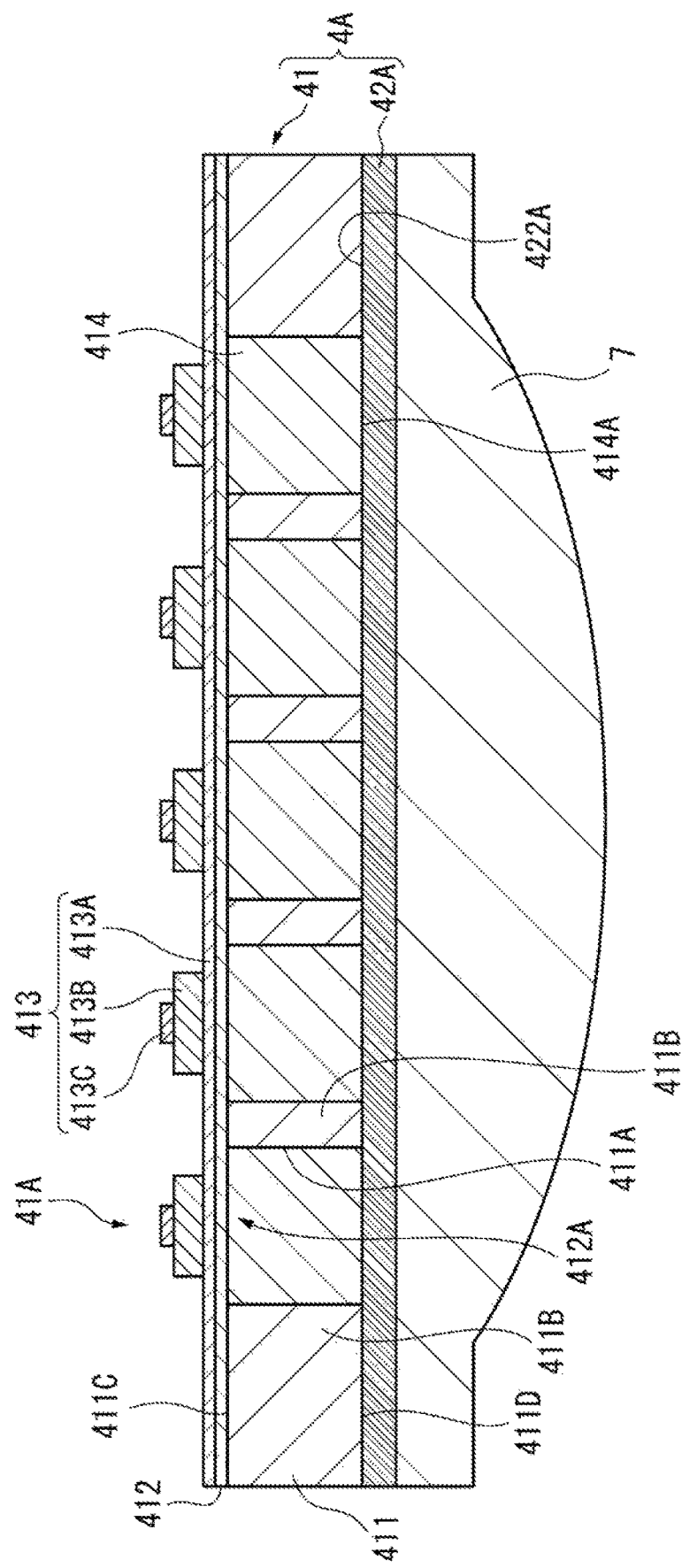
FIG. 8 is a sectional view illustrating an ultrasonic substrate of an ultrasonic apparatus according to a second embodiment of the invention.

FIG. 8 is a sectional view illustrating a schematic configuration of an ultrasonic device 4A according to the second embodiment. Also in FIG. 8, for convenience of description, the number of the arranged ultrasonic transducers 41A is small; however, more ultrasonic transducers 41A are actually arranged.

In the embodiment, as illustrated in FIG. 8, the ultrasonic device 4A has the metal membrane 42A, instead of the metal membrane 42. The metal membrane 42A is provided on the substantially entire region in the second surface 411D of the ultrasonic substrate 41. In other words, the metal membrane 42A is provided on the partition 411B corresponding to an unopened region and a region of the acoustic layer 414, with which the opening 411A is filled, and on regions of the second surface 411D corresponding to the partition and the region of the acoustic layer.

Here, in the embodiment, after the opening 411A is filled with the acoustic layer 414, the surface is leveled to be an evenly flat surface so as to flush with the second surface 411D of the element substrate 411 by using a member such as a spatula having linear portion. Hence, the surface 414A of the acoustic layer 414 on the opposite side to the element substrate 411 is a surface that is continued flat to the second surface 411D and corresponds to a back surface 422A of the metal membrane 42A. In other words, the surface 414A of the acoustic layer 414 is flush with the back surface 422A of the metal membrane 42A. Hence, the metal membrane 42A can be formed on the element substrate 411 and the acoustic layer 414 to have a uniform thickness without a step. Accordingly, even in a case where the acoustic lens 7 is provided on the metal membrane 42, an occurrence of mixing of the gases between the acoustic lens 7 and the metal membrane 42A is reduced.

In the embodiment, the metal membrane 42A is provided in the substantially entire region of the second surface 411D through a process of vapor deposition or the like; however, the disposition is not limited thereto, and the metal membrane 42A may be provided on the second surface 411D through sputtering or the like, for example.

Figure 9:
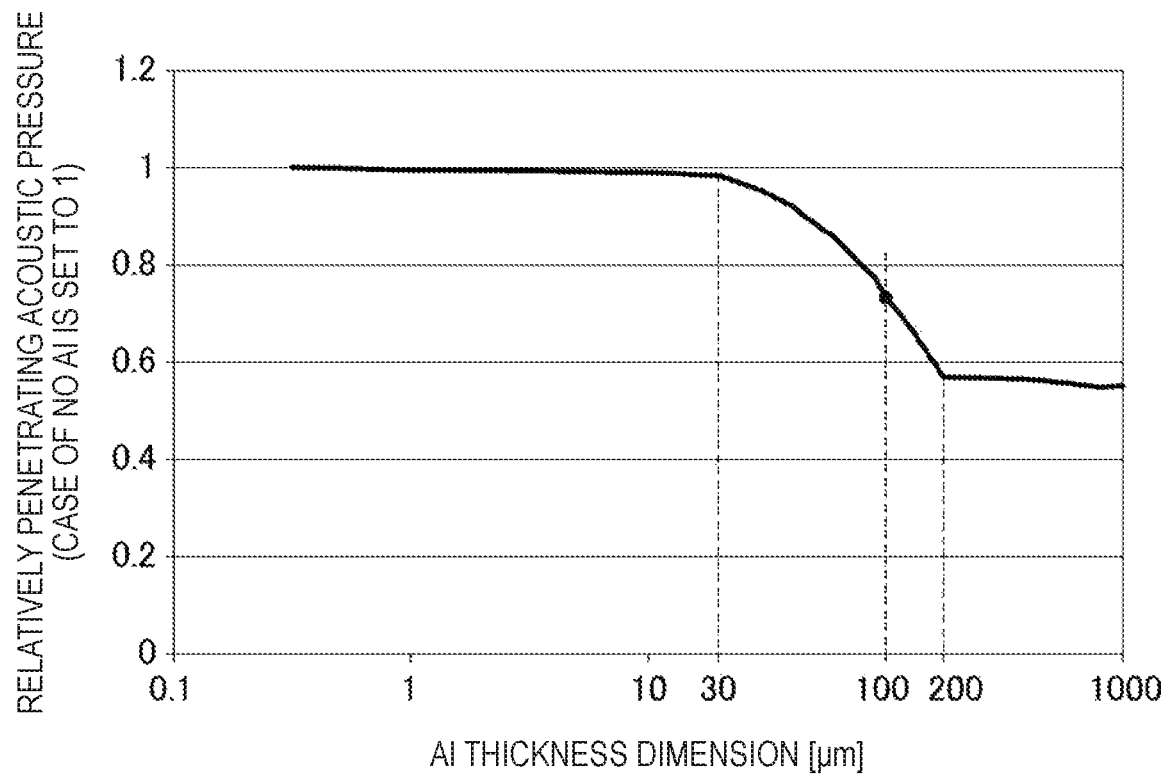
FIG. 9 is a graph illustrating relatively penetrating acoustic pressure depending on a thickness dimension of a shield membrane according to the second embodiment.

FIG. 9 is a graph illustrating a relationship between a thickness (membrane-thickness dimension) of the metal membrane 42A and relatively penetrating acoustic pressure of the ultrasonic wave. In FIG. 9, the relatively penetrating acoustic pressure of the ultrasonic waves is "1" in a case where the metal membrane 42A is not provided.

In addition, a relationship between the membrane-thickness dimension of the metal membrane 42A and the relatively penetrating acoustic pressure of the ultrasonic wave indicates acoustic pressure obtained by setting an acoustic pressure measurement point in the acoustic lens 7 and measuring a pulse wavelength (ultrasonic waves) of 5 MHz at the acoustic pressure measurement point via the acoustic layer 414 and the metal membrane 42A with which the opening 411A is filled.

The metal membrane 42A that is made of, for example, aluminum has characteristics of effectively reducing the electromagnetic wave from outside which is noise when the ultrasonic waves are transmitted and received as the membrane-thickness dimension of the metal membrane 42A increases.

Incidentally, the electromagnetic shield effect due to the metal membrane 42A is increased as the membrane-thickness dimension of the metal membrane 42A is increased; however, the membrane-thickness dimension is increased, a value of the relatively penetrating acoustic pressure is reduced.

Accordingly, in the embodiment, in a case where Al is used as the metal membrane 42A, it is preferable that the membrane-thickness dimension is 10 μm or larger and 200 μm or small.

Here, as illustrated in FIG. 9, in a case where the membrane-thickness dimension of the metal membrane 42A is smaller than 10 μm, the value of the relatively penetrating acoustic pressure is a value close to "1", and thus it is possible to cause the ultrasonic waves emitted from the ultrasonic transducers 41A to reliably penetrate through the metal membrane. However, an amount of the electromagnetic waves absorbed by the metal membrane 42A is also reduced.

In addition, in the ultrasonic apparatus 1, in order to obtain a clear internal tomographic image, it is necessary to secure the relatively penetrating acoustic pressure of the ultrasonic waves of 0.5 or higher. However, when the membrane-thickness dimension of the metal membrane 42A exceeds 200 μm, the relatively penetrating acoustic pressure is 0.5 or lower (a decrease rate of the relatively penetrating acoustic pressure is 0.5 or higher).

In this respect, as described above, in the embodiment, the membrane-thickness dimension of the metal membrane 42A is 10 μm or larger and 200 μm or smaller, that is, the membrane-thickness dimension of the metal membrane 42A is designed to a dimension such that the decrease rate of the relatively penetrating acoustic pressure of the ultrasonic waves is 0.5 or lower. Thus, it is possible to sufficiently cut the electromagnetic waves from outside, and it is possible to secure the relatively penetrating acoustic pressure which is 0.5 or larger.

In addition, the membrane-thickness dimension of the metal membrane 42A is preferably 10 μm or larger and 100 μm or smaller, and more preferably, 10 μm or larger and 30 μm or smaller. As illustrated in FIG. 9, when the membrane-thickness dimension is larger than 100 μm, the relatively penetrating acoustic pressure of the metal membrane 42A has steep width of decrease (gradient), and thus acoustic characteristics of the ultrasonic waves are unstable. In this respect, the metal membrane 42A has the membrane-thickness dimension of 100 μm or smaller, and thereby acoustic characteristics of the ultrasonic waves are unlikely to remarkably change. Thus, it is possible to provide the ultrasonic device 4A having stable acoustic characteristics.

Further, in a range where the membrane-thickness dimension of the metal membrane 42A is 10 μm or larger and 30 μm or smaller, the relatively penetrating acoustic pressure is not almost changed. Therefore, the membrane-thickness dimension of the metal membrane 42A is 10 μm or larger and 30 µm or smaller, and thereby it is possible to provide the ultrasonic device 4A having very stable acoustic characteristics.

Effect of Second Embodiment

The ultrasonic apparatus according to the embodiment described above has the following effects, as well as the same effects as those of the ultrasonic apparatus 1 according to the first embodiment.

In the embodiment, the metal membrane 42A is provided in a region of the acoustic layer 414, and thereby it is possible to more effectively reduce an amount of the electromagnetic waves from outside. On the other hand, in this manner, when the metal membrane 42A is provided in the region of the acoustic layer 414 on a traveling route of the ultrasonic waves, the metal membrane interferes with the transmission and reception of the ultrasonic waves. In this respect, in the embodiment, the metal membrane 42A has the thickness dimension of 10 µm or larger and 200 µm or smaller. In such a configuration, the decrease rate of the relatively penetrating acoustic pressure of the ultrasonic waves is 0.5 or lower due to the metal membrane 42A, and thus it is possible to reduce the occurrence of a significant decrease in transmission and reception efficiency of the ultrasonic waves.

In addition, in the embodiment, it is preferable that the metal membrane 42A has the thickness dimension of 10 µm or larger and 100 µm or smaller. The metal membrane 42A has the thickness dimension of 10 µm or larger. In this manner, it is possible to sufficiently absorb the electromagnetic waves, and it is possible to reduce an occurrence of a problem in which noise electromagnetic waves which have penetrated through the metal membrane 42A are input to the piezoelectric element 413, for example. In addition, when the metal membrane 42A has the membrane-thickness dimension larger than 100 µm, a width of decrease (gradient) of the relatively penetrating acoustic pressure is steep, and thus acoustic characteristics of the ultrasonic waves are unstable. In this respect, the metal membrane 42A has the membrane-thickness dimension of 100 µm or smaller, and thereby acoustic characteristics of the ultrasonic waves are unlikely to remarkably change. Thus, it is possible to provide the ultrasonic device 4A having stable acoustic characteristics.

Further, in a case where the thickness dimension of the metal membrane 42A is 10 µm or larger and 30 µm or smaller, the relatively penetrating acoustic pressure is not almost changed. Therefore, it is possible to provide the ultrasonic device 4A having very stable acoustic characteristics.

In the embodiment, the acoustic layer 414 is provided with the surface 414A which is flush with the back surface 422A of the metal membrane 42A. Therefore, when the acoustic lens 7 is bonded to the back surface 422A of the metal membrane 42A and the surface 414A, it is possible to reduce an occurrence of a problem in which gases such as the air are mixed between the metal membrane 42A and the acoustic lens 7.

In the embodiment, the dimension of the metal membrane 42A in the thickness direction of the ultrasonic substrate 41 is designed such that the decrease rate of relatively penetrating acoustic pressure of the ultrasonic waves is 0.5 or lower. In this manner, a decrease rate of the relatively penetrating acoustic pressure of the ultrasonic waves is 0.5 or lower due to the metal membrane 42A, and thus it is possible to provide the metal membrane 42A due to which it is possible to reduce the occurrence of a significant decrease in transmission and reception efficiency of the ultrasonic waves.

In addition, after the opening 411A of the element substrate 411 is formed by being filled with the acoustic layer 414, the metal membrane 42A is formed. Then, since it is not necessary to perform shape processing of the metal membrane 42A through patterning or the like, it is possible to improve the manufacturing efficiency.

Third Embodiment

Next, a third embodiment of the invention will be described.

In the first embodiment described above, an example in which the metal membrane 42 is positioned on the partition 411B and a region on the second surface 411D of the ultrasonic substrate 41 which corresponds to the partition, that is, an example in which the metal membrane 42 is positioned on the partition 411B so as to surround an end edge of the opening 411A, is described.

In this respect, the third embodiment differs from the first embodiment in that a metal membrane 42B is provided in a substantially entire region in the opening 411A, as well as on the second surface 411D corresponding to the partition 411B which corresponds to the partition.

Figure 10:
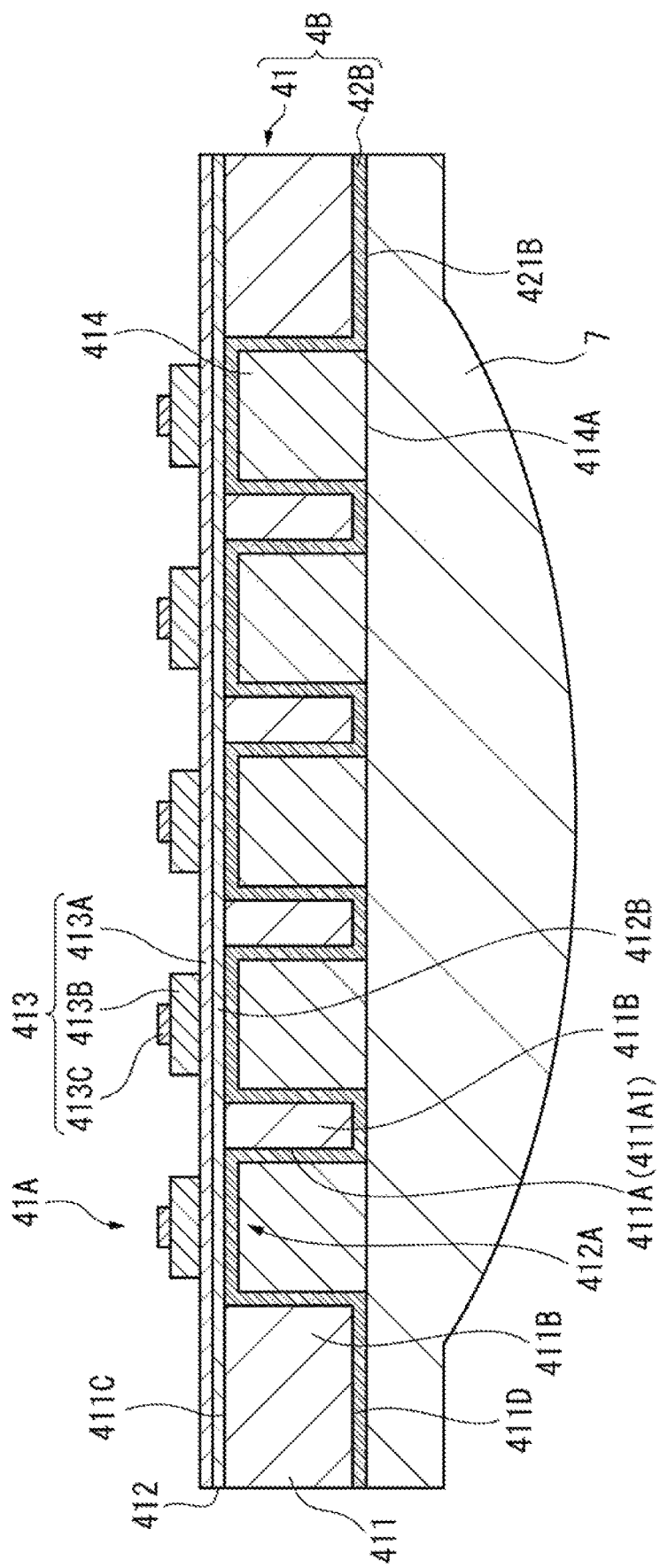
FIG. 10 is a sectional view illustrating an ultrasonic substrate of an ultrasonic apparatus according to a third embodiment of the invention.

FIG. 10 is a sectional view illustrating a schematic configuration of an ultrasonic device 4B according to a third embodiment. Also in FIG. 10, for convenience of description, the number of the arranged ultrasonic transducers 41A is reduced; however, more ultrasonic transducers 41A are actually arranged.

In the embodiment, as illustrated in FIG. 10, the ultrasonic device 4B has the metal membrane 42B, instead of the metal membrane 42. The metal membrane 42B is provided on a part of the opening 411A and the support membrane 412 as well as on the second surface 411D corresponding to the partition 411B of the ultrasonic substrate 41 which corresponds to the partition. In other words, the metal membrane 42B is provided on the partition 411B corresponding to the unopened region on the second surface 411D, on an inner circumferential surface 411A1 of the opening 411A, and on a surface 412B of the support membrane 412, which faces the opening 411A. In other words, the metal membrane 42B is provided to be positioned between the acoustic layer 414 with which the opening 411A is filled, the inner circumferential surface 411A1 and the surface 412B, and to surround the opening 411A.

After the metal membrane 42B is vapor-deposited on the element substrate 411, the opening 411A, on which the metal membrane 42B is vapor-deposited, is filled with the liquid-phase material (for example, a liquid-phase silicone) that forms the acoustic layer 414, and the acoustic layer 414 is formed by leveling a front surface thereof to be even by using a member such as a spatula having a linear portion. Accordingly, the acoustic layer 414 is provided with the surface 414A that is continued flat to a front surface 421B of the metal membrane 42B without a step. Therefore, when the acoustic lens 7 is bonded to the front surface 421B of the metal membrane 42B and the surface 414A, it is possible to reduce the occurrence of a problem in which gases such as the air are mixed between the acoustic layer 414 and the acoustic lens 7.

In addition, in the embodiment, the metal membrane 42B is provided on the partition 411B, the inner circumferential surface 411A1, and the surface 412B through a process of vapor deposition or the like; however, the process is not limited thereto, and the metal membrane 42B may be provided through sputtering or the like, for example.

Here, as described above, a portion of the support membrane 412, which blocks the opening 411A, configures the vibrating portion 412A, and the vibrating portion 412A and the piezoelectric elements 413 configure one ultrasonic transducer 41A (vibrator). In other words, in the embodiment, a part of the metal membrane 42B which is in contact with the surface 412B of the support membrane 412 also configures the vibrating portion 412A. Therefore, in the embodiment, it is preferable that the metal membrane 42B has the thickness dimension (membrane-thickness dimension) of 10 μm or larger and smaller than 50 μm, and is set to 30 μm in the embodiment, for example. In this manner, the ultrasonic waves are appropriately emitted from the ultrasonic transducers 41A.

Effect of Third Embodiment

The ultrasonic apparatus according to the embodiment described above has the following effects, as well as substantially the same effects as those of the ultrasonic apparatus 1 according to the first embodiment.

In the embodiment, the metal membrane 42B is provided in the unopened region (partition 411B) on the second surface 411D of the ultrasonic substrate 41, on the inner circumferential surface 411A1 of the opening 411A, and on the surface 412B of the support membrane 412, which faces the opening 411A. As described above, the metal membrane 42B provided on the partition 411B which is the unopened region on the second surface 411D of the ultrasonic substrate 41 has a weak influence on the transmission and reception of the ultrasonic waves. Similarly, the metal membrane 42B provided on the inner circumferential surface 411A1 of the opening 411A does not interrupt the traveling of the ultrasonic waves and has a weak influence on the transmission and reception of the ultrasonic waves. In addition, the metal membrane 42B provided on the support membrane 412 vibrates along with the support membrane 412 in accordance with transmission and reception processing of the ultrasonic waves. Therefore, the metal membrane 42B has a sufficiently small thickness dimension to the extent (for example, 10 μm or larger and smaller than 50 μm) that the metal membrane does not interfere with the vibration of the support membrane 412, and thereby it is possible to reduce an influence on the transmission and reception of the ultrasonic waves even with the metal membrane 42B provided on the support membrane 412. In other words, also in the embodiment, it is possible to reduce the occurrence of a decrease in the transmission and reception efficiency of the ultrasonic waves due to the metal membrane 42B, and it is possible to cover a broad range with the metal membrane 42B. Therefore, it is possible to further reduce an influence of noise from the electromagnetic waves.

Modification of Embodiment

The invention is not limited to the embodiments described above, and the invention also includes a configuration obtained through modification, improvement, and an appropriate combination of the embodiments in a range in which it is possible to achieve the object of the invention.

In the embodiments, the acoustic lens 7 is provided; however, the configuration is not limited thereto. For example, a configuration in which the sensor window 21B is sealed with an acoustic member having the same or substantially the same acoustic impedance as that of the living body, and the acoustic layer 414 is provided between the acoustic member and the ultrasonic substrate 41 may be employed.

In the embodiments, the metal membranes 42, 42A, and 42B are each formed of nickel, gold, copper, or the like, as well as aluminum (Al); however, the embodiments are not limited thereto. For example, the metal membrane 42, 42A, or 42B may be formed of Fe, Sn, or the like.

The above second embodiment employs a configuration in which the surface 414A of the acoustic layer 414 is configured to be flush with the second surface 411D of the element substrate 411, as an example; however, the configuration is not limited thereto.

Figure 11:
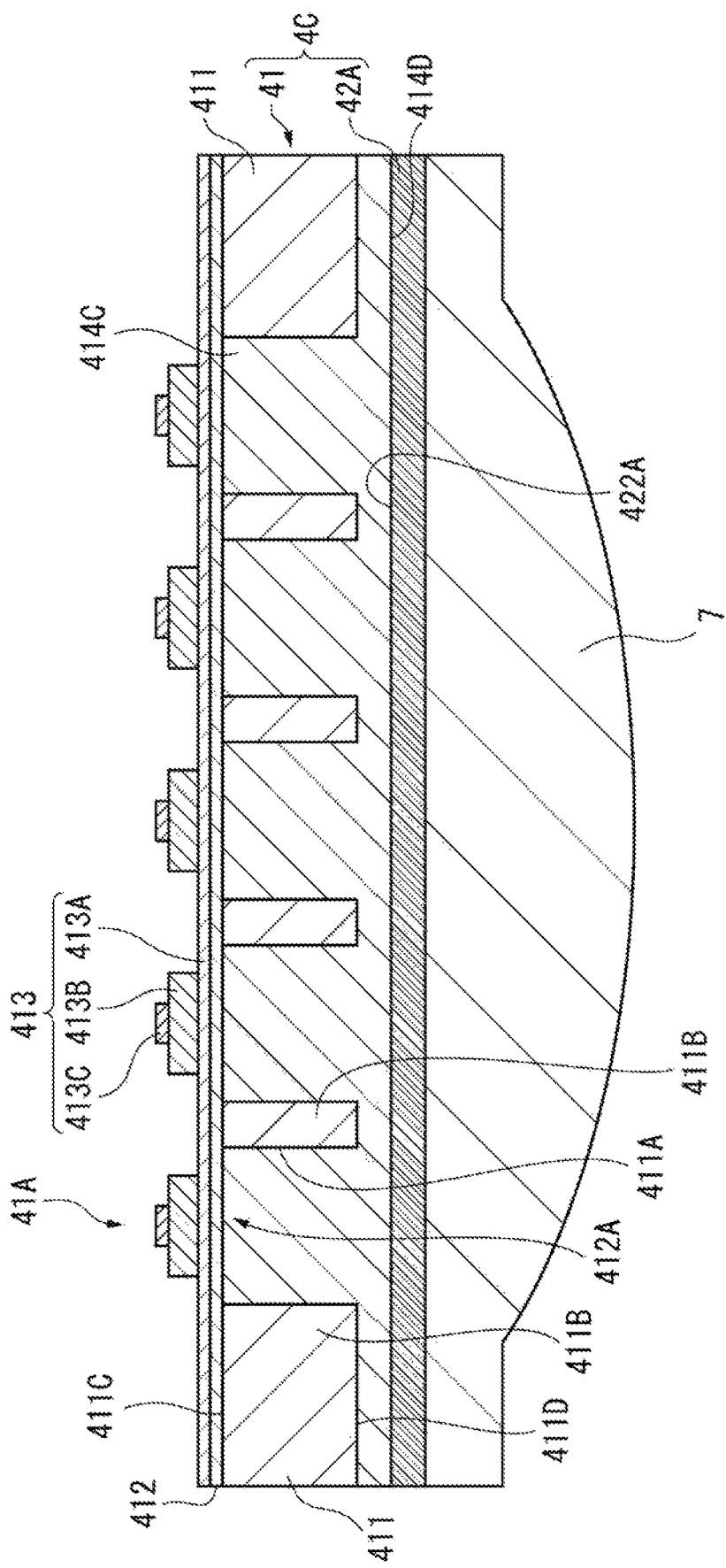
FIG. 11 is a sectional view illustrating an ultrasonic device according to the above second embodiment.

FIG. 11 is a sectional view illustrating an ultrasonic device 4C according to a modification example of the second embodiment.

As illustrated in FIG. 11, the ultrasonic device 4C includes an acoustic layer 414C, instead of the acoustic layer 414. As illustrated in FIG. 12, the acoustic layer 414C is provided to cover the second surface 411D (partition 411B) from the opening 411A. In this case, a front surface 414D of the acoustic layer 414C is leveled to have an even flat surface at a position apart from the second surface 411D by a predetermined dimension. In this manner, since the front surface of the acoustic layer 414C is a flat surface, it is possible to form the metal membrane 42A to be even on the acoustic layer 414C.

In addition, the first embodiment is the same as the third embodiment, and an example in which the acoustic layer 414 is provided with the surface 414A that is flush with the front surface 421 of the metal membrane 42, or the front surface 421B of the metal membrane 42B is described; however, the embodiments are not limited thereto.

For example, the acoustic layer 414 may be provided to cover the metal membrane 42 (metal membrane 42B) from inside the opening 411A. In this case, the front surface of the acoustic layer 414 is leveled to have an even flat surface at a position apart from the metal membrane 42 by a predetermined dimension. In this manner, since the front surface of the acoustic layer 414 is a flat surface, the occurrence of mixing of the air is reduced even in a case where the acoustic member such as the acoustic lens 7 is provided, and thus the acoustic member can be brought into close contact with the acoustic layer 414.

In the modification example of the first embodiment, the metal membrane 42 is only provided on the outer edge in the partition 411B (unopened portion), and the region thereof extending in the direction parallel to the X direction; however, the example is not limited thereto. For example, instead of the region extending in the direction parallel to the X direction, the metal membrane 42 may be provided in a region extending in a direction parallel to the Y direction. Further, the metal membrane 42 may be provided to surround the two openings 411A, or the metal membrane 42 may be provided to surround the four openings 411A. In other words, the metal membrane 42 may be disposed at any position of the partition 411B to have an opening dimension which is equal to or smaller than the half wavelength of the electromagnetic wave.

In the second embodiment, the metal membrane 42A is provided on the second surface 411D through a process of vapor deposition or the like; however, the embodiment is not limited thereto. For example, the metal membrane 42A may be provided on the acoustic lens 7 through the process of vapor deposition or the like. In addition, the metal membrane 42A may be provided on the acoustic lens 7 through the process of sputtering or the like. In other words, in the second embodiment, anyone of the second surface 411D and the acoustic lens 7 may be provided with the metal membrane.

In the third embodiment, the metal membrane 42B is provided on the partition 411B corresponding to the unopened region on the second surface 411D, on the inner circumferential surface 411A1 of the opening 411A, and on the surface 412B of the support membrane 412, which faces the opening 411A; however, the embodiment is not limited thereto. For example, the metal membrane 42B may be provided in any one of the inner circumferential surface 411A1 of the opening 411A or the surface of the support membrane 412 which faces the opening 411A, as well as the partition 411B.

In addition, the metal membrane may be provided in the surface 412B of the support membrane 412 which faces the opening 411A, in a part of the partition 411B, and a part of the inner circumferential surface 411A1 of the opening 411A. In other words, metal membranes for shielding, which are provided in the surface 412B that faces the opening 411A, may be configured to be connected to each other, and to be conductive to GND.

The embodiments employ an example in which the opening 411A is configured to have a rectangular shape when viewed in the thickness direction of the ultrasonic substrate 41; however, the embodiment is not limited thereto. For example, a circular shape may be formed, or another polygonal shape may be formed.

In the embodiments, a configuration in which the support membrane 412 and the piezoelectric elements 413 as the ultrasonic element that vibrates the support membrane 412 are provided as the ultrasonic transducer 41A is described. However, the embodiments are not limited thereto; and the ultrasonic element other than piezoelectric element may be used. For example, an ultrasonic element or the like in which the vibrating membrane is disposed on the substrate via an air gap, an electrostatic actuator is disposed between the substrate and the vibration membrane, and thereby the vibration membrane is vibrated may be used.

In addition, the ultrasonic transducer 41A does not have the vibration membrane, but may be configured to transmit the ultrasonic waves by vibrating the vibrator such as the piezoelectric element.

In the embodiments described above, the ultrasonic apparatus 1 with the inside of the living body as the measurement target is described; however, the embodiment is not limited thereto. For example, the invention can be applied to an ultrasonic apparatus that detects a defect of a structure, with various types of structures as the measurement target, and checks for aging. In addition, the invention can also be applied to an ultrasonic apparatus that detects a defect of a measurement target, with semiconductor package, a wafer, or the like as the measurement target.

In addition, the specific structure of the embodiment of the invention may be configured by appropriately combining the embodiments and modification examples in a range in which it is possible to achieve the object of the invention, and may be appropriately modified to have another structure.

The entire disclosure of Japanese Patent Application No. 2016-231418 filed on Nov. 29, 2016 is expressly incorporated by reference herein.

What is claimed is:

1. An ultrasonic device comprising:
   a substrate that is provided with a first surface and a second surface opposite to each other, the substrate having a plurality of through holes opened from the first surface to the second surface, the plurality of through holes having first openings at the first surface and second openings at the second surface;
   a support disposed on the first surface of the substrate, the support closing the first openings of the plurality of through holes;
   a vibrator provided on the support; and
   a metal membrane disposed on an entirety of the second surface of the substrate.

2. The ultrasonic device according to claim 1, further comprising:
   an acoustic layer provided in the plurality of through holes,
   wherein the metal membrane is further disposed on the acoustic layer located at the second openings, and
   wherein the metal membrane has a thickness dimension of 10 µm or larger and 200 µm or smaller in a thickness direction of the substrate.

3. The ultrasonic device according to claim 2,
   wherein the metal membrane has the thickness dimension of 10 µm or larger and 100 µm or smaller.

4. The ultrasonic device according to claim 1,
   wherein the metal membrane is further disposed on an inner circumferential surface of the plurality of through holes and on a surface of the support facing the first openings.

5. The ultrasonic device according to claim 1, further comprising:
   an acoustic layer provided in the plurality of through holes,
   wherein the acoustic layer has a surface that is continued flat to a surface of the metal membrane.

6. An ultrasonic apparatus comprising:
   an ultrasonic device including:
      a substrate that is provided with a first surface and a second surface opposite to each other, the substrate having a plurality of through holes opened from the first surface to the second surface, the plurality of through holes having first openings at the first surface and second openings at the second surface;
      a support disposed on the first surface of the substrate, the support closing the first openings of the plurality of through holes;
      a vibrator provided on the support; and
      a metal membrane disposed on an entirety of the second surface of the substrate; and
   a controller configured to control the ultrasonic device.

7. The ultrasonic apparatus according to claim 6, further comprising:
   an acoustic layer provided in the plurality of through holes,
   wherein the metal membrane is further disposed on the acoustic layer located at the second openings, and
   wherein the metal membrane has a thickness dimension of 10 µm or larger and 200 µm or smaller in a thickness direction of the substrate.

8. The ultrasonic apparatus according to claim 7,
   wherein the metal membrane has the thickness dimension of 10 µm or larger and 100 µm or smaller.

9. The ultrasonic apparatus according to claim 6,
   wherein the metal membrane is further disposed on an inner circumferential surface of the plurality of through holes and on a surface of the support facing the first openings.

10. The ultrasonic apparatus according to claim 6, further comprising:

an acoustic layer provided in the plurality of through holes, wherein the acoustic layer has a surface that is continued flat to a surface of the metal membrane.

* * * * *